United States Patent [19]

Tucker et al.

[11] Patent Number: 5,719,154
[45] Date of Patent: Feb. 17, 1998

[54] OXAZOLIDINONE ANTIBACTERIAL AGENTS HAVING A SIX-MEMBRANE HETEROAROMATIC RING

[76] Inventors: John A. Tucker, 3721 Greenleaf Cir., Apt. 301, Kalamazoo, Mich. 49006; Steven J. Brickner, 9 Fargo Dr., Ledyard, Conn. 06339; Debra A. Ulanowicz, 1320 W. Maple St., Kalamazoo, Mich. 49008

[21] Appl. No.: 762,478

[22] Filed: Dec. 9, 1996

Related U.S. Application Data

[60] Provisional application No. 60/008,554, Dec. 13, 1995.
[51] Int. Cl.$^6$ .................. C07D 403/04; A61K 31/50; A61K 31/505
[52] U.S. Cl. .................. 514/252; 544/238; 544/295
[58] Field of Search .................. 544/295, 238; 514/252

[56] References Cited

U.S. PATENT DOCUMENTS

| | | | |
|---|---|---|---|
| 5,547,950 | 8/1996 | Hutchinson et al. | 514/252 |
| 5,556,873 | 9/1996 | Huang et al. | 514/407 |
| 5,609,996 | 3/1997 | Tang et al. | 430/386 |

FOREIGN PATENT DOCUMENTS

| | | |
|---|---|---|
| 0601665 | 7/1992 | Japan . |
| 92/23384 | 5/1992 | WIPO . |
| 93 09103A | 5/1993 | WIPO . |
| 93 23384A | 11/1993 | WIPO . |
| 95 14684A | 6/1995 | WIPO . |

OTHER PUBLICATIONS

Derwent Abstracts 3,033,157, May 1992.

*Primary Examiner*—Matthew V. Grumbling
*Attorney, Agent, or Firm*—Lucy X. Yang

[57] ABSTRACT

This invention provides a novel oxazolidinone derivative represented by Formula I or pharmaceutical acceptable salts thereof:

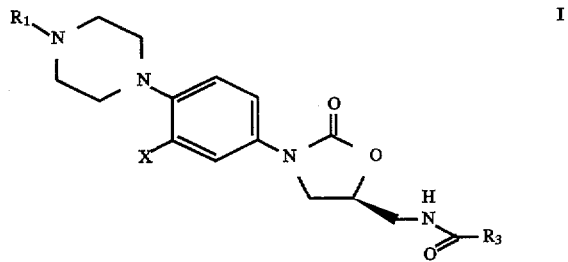

wherein $R_1$ is substituted or unsubstituted 2-pyrimidinyl, 4-pyrimidinyl, or 3-pyridazinyl; X is hydrogen or fluoro; $R_3$ is $C_{1-4}$ alkyl, $C_{1-4}$ alkoxy, $C_{3-6}$ cycloalkyl or $C_{1-4}$ alkylamino or dialkylamino. The compounds are useful antimicrobial agents.

12 Claims, No Drawings

OXAZOLIDINONE ANTIBACTERIAL AGENTS HAVING A SIX-MEMBRANE HETEROAROMATIC RING

BACKGROUND OF THE INVENTION

Cross-reference to Related Application

This application claims the benefit of the following provisional application: U.S. Ser. No. 60/008,554, filed Dec. 13, 1995, under 35 USC 119(e)(i).

FIELD OF THE INVENTION

This invention relates to novel oxazolidinone derivatives or pharmaceutically acceptable salts thereof. Particularly, this invention relates to oxazolidinone derivatives which have a six-membered heteroaromatic ring containing two nitrogen atoms.

BACKGROUND OF THE INVENTION

The compounds of the present invention are useful antimicrobial agents, effective against a number of human and veterinary pathogens, including grampositive aerobic bacteria such as multiply-resistant *staphylococci* and *streptococci*, as well as anaerobic organisms such as *bacteroides* and *clostridia* species, and acid-fast organisms such as *Mycobacterium tuberculosis* and *Mycobacterium avium*.

The compounds are particularly useful because they are effective against the latter organisms which are known to be responsible for infection in persons with AIDS.

INFORMATION DISCLOSURE

International Publication No. WO93/23384 discloses oxazolidinones containing phenyl and pyridyl substituents on the piperazine moiety and their uses as antimicrobials.

Derwent Abstracts 3,033,157 discloses aminocyclopropyl-oxo-1,4-dihydro-naphthyridine-3-carboxylic acid and their use as antibacterial and growth promoter.

Abstracts of Japanese Patent 0,601,665 disclose antimicrobial quinolone-3-carboxylic acid derivatives useful as antibacterial agents effective against gram positive and gram negative bacteria and their resistant strains.

SUMMARY OF THE INVENTION

This invention provides a novel oxazolidinone derivative represented by the

Formula I:

or pharmaceutically acceptable salts thereof wherein $R_1$ is (a)

(b)

(c)

$R_2$ is (a) hydrogen, or (b) $C_{1-4}$ alkyl;

$R_3$ is (a) $C_{1-4}$ alkyl, (b) $C_{3-6}$ cycloalkyl, (c) $C_{1-4}$ alkoxy, (d) $C_{1-4}$ alkylamino, or (e) $C_{1-4}$ dialkylamino; and X is (a) hydrogen, or (b) fluoro.

This invention provides novel oxazolidinone derivatives useful as preventatives and therapeutics for infectious diseases. The compounds of this invention have excellent antimicrobial action against various human and veterinary pathogens, including multiply-resistant *staphylococci* and *streptococci*, as well as anaerobic organisms such as *bacteroides* and *clostridia species*, and acid-fast *Mycobacterium tuberculosis* and *Mycobacterium avium*.

DETAILED DESCRIPTION OF THE INVENTION

For the purpose of the present invention, the carbon content of various hydrocarbon containing moieties is indicated by a prefix designating the minimum and maximum number of carbon atoms in the moiety; i.e., the prefix $C_{i-j}$ defines the number of carbon atoms present from the integer "i" to the integer "j", inclusive.

The term "$C_{1-4}$ alkyl" refers to methyl, ethyl, n-propyl, n-butyl, and isomeric forms thereof.

The term "$C_{1-4}$ alkoxy" refers to an alkyl group having 1 to 4 carbon atoms attached to a hydroxy moiety; for example, methoxy, ethoxy, n-propyloxy, n-butyloxy and isomeric forms thereof.

The term "$C_{3-6}$ cycloalkyl" refers to cyclopropyl, cyclobutyl, cyclopentyl, cyclohexyl and isomeric forms thereof, and preferably a cycloalkyl group having 4 to 6 carbon atoms.

The term "$C_{1-4}$ alkylamino" refers to an alkyl group having 1 to 4 carbon atoms attached to an amino moiety; for example, methylamino, ethylamino, n-propylamino, n-butylamino and isomeric forms thereof.

The term "$C_{1-4}$ dialkylamino" refers to two alkyl groups having 1 to 4 carbon atoms attached to an amino moiety; for example, dimethylamino, methylethylamino, diethylamino, dipropylamino, methypropylamino, ethylpropylamino, dibutylamino and isomeric forms thereof.

The compounds of the present invention can be converted to their salts according to conventional methods.

The term "pharmaceutically acceptable salts" refers to salts useful for administering the compounds of this invention. These salts include hydrochloride, hydrobromide, hydroiodide, sulfate, phosphate, acetate, propionate, lactate, mesylate, maleate, malate, succinate, tartrate, citrate, 2-hydroxyethyl sulfonate, fumarate and the like. These salts may be in hydrated form. Some of the compounds of this invention may form metal salts such as sodium, potassium, calcium and magnesium salts and they are embraced by the term "pharmaceutically acceptable salts".

In a preferred embodiment of the N-phenyloxazolidinone compounds of the present invention, the preferred $R_1$ is substituted or unsubstituted 3-pyridazinyl. The most preferred $R_1$ is 3-(6-methylpyridazinyl). The preferred $R_3$ is methyl. The preferred X is fluoro.

The preferred absolute configuration at C-5 of the oxazolidinone ring of compounds claimed in this invention is as represented in the structure of Formula I. This absolute configuration is called (S) under the Cahn-Ingold-Prelog nomenclature system. It is this (S)-enantiomer which is pharmacologically active. The racemic mixture is useful in the same way and for the same purpose as the pure (S)-enantiomer; the difference is that twice as much racemic material must be used to produce the same antibacterial effect.

The compounds represented by the general Formula I can be prepared by the method of reaction in Scheme I.

As shown in Scheme I, amine 1 is reacted with a heteroaromatic compound 2 in a suitable solvent such as dimethylacetamide, dimethylformamide, ethanol, or ethylene glycol at a suitable temperature in the range of −78° C. to 180° C. to afford compounds of Formula I. The presence of a suitable base such as diisopropylethyl amine is useful in some cases to improve the yield of the reaction. The starting compounds of amine 1 can be prepared according to the procedures described in International Publication No. WO93/23384. The Y group of structure 2 is a suitable leaving group well known to one of ordinary skill in the art such as fluoro, chloro, bromo, —$SCH_3$, —$SO_2CH_3$, or —$OC_6H_5$, etc.

The compounds of the present invention include the followings:

1. (S)-N-[[3-[-3-fluoro-4-[4-(2-pyrimidinyl)-1-piperazinyl]phenyl-2-oxo-5-oxazolidinyl]methyl] acetamide;
2. (S)-N-[[3-[-3-fluoro-4-[4-(4-pyrimidinyl)-1-piperazinyl]phenyl-2-oxo-5-oxazolidinyl]methyl] acetamide;
3. (S)-N-[[3-[-3-fluoro-4-[4-(3-pyridazinyl)-1-piperazinyl]phenyl-2-oxo-5-oxazolidinyl]methyl] acetamide; and
4. (S)-N-[[3-[-3-fluoro-4-[4-(3-(6-methylpyridazinyl))-1-piperazinyl]phenyl-2-oxo-5-oxazolidinyl]methyl] acetamide.

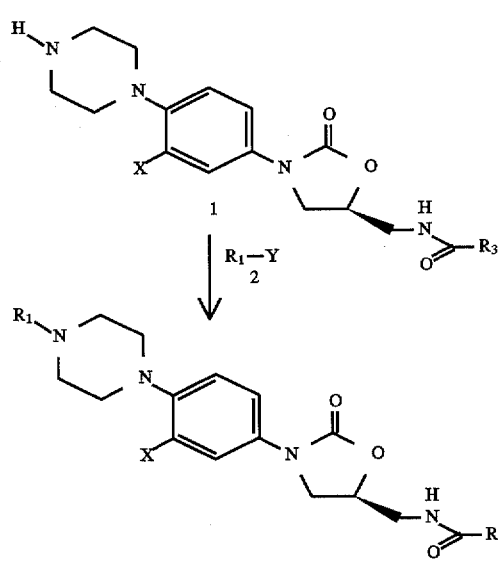

The pharmaceutical compositions of this invention may be prepared by combining the compounds of Formula I of this invention with a solid or liquid pharmaceutically acceptable carrier, and optionally, with pharmaceutically acceptable adjuvants and excipients employing standard and conventional techniques. Solid form compositions include powders, tablets, dispersible granules, capsules and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water, water-propylene glycol, and water-polyethylene glycol systems, optionally containing conventional coloring agents, flavoring agents, stabilizers and thickening agents.

The pharmaceutical composition is provided by employing conventional techniques. Preferably the composition is in unit dosage form containing an effective amount of the active component, that is, the compounds of Formula I according to this invention.

The quantity of active component, that is, the compounds of Formula I according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

In therapeutic use for treating bacterial infections in humans and other animals that have been diagnosed with bacterial infections, the compounds or pharmaceutical compositions thereof will be administered orally, parenterally and/or topically at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100 mg/kg, more preferably about 3.0 to about 50 mg/kg of body weight/day. It is to be understood that the dosages may vary depending upon the requirements of the patient, the severity of the bacterial infection being treated, and the particular compounds being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

These compounds are useful for the treatment of microbial infections in humans and other warm blooded animals by either parenteral, oral, or topical administration. In general, the preferred form of administration is orally. Pharmaceutical compositions for parenteral administration will generally contain a pharmaceutically acceptable amount of the compounds according to Formula I as a soluble salt (acid addition salt or base salt) dissolved in a pharmaceutically acceptable liquid carrier such as, for example, water-for-injection and a suitably buffered isotonic solution having a pH of about 3.5–6. Suitable buffering agents include, for example, trisodium orthophosphate, sodium bicarbonate, sodium citrate, N-methylglucamine, L(+)-lysine and L(+)-arginine, to name a few. The compounds according to Formula I generally will be dissolved in the carrier in an amount sufficient to provide a pharmaceutically acceptable injectable concentration in the range of about 1 mg/mi to about 400 mg/ml. The resulting liquid pharmaceutical composition will be administered so as to obtain the above-mentioned antibacterially effective amount of dosage. The compounds of Formula I according to this invention are advantageously administered orally in solid and liquid dosage forms.

The compounds of this invention are useful antimicrobial agents, effective against various human and veterinary pathogens, including multiply-resistant *staphylococci* and *streptococci*, as well as anaerobic organisms such as *bacteroides* and *clostridia* species, and acid-resistant organisms such as *Mycobacterium tuberculosis* and *Mycobacterium avium*. Humans or animals infected with such pathogens are readily diagnosed by a physician or veterinarian of ordinary skill.

Antimicrobial activity is tested in vivo using the Murine Assay procedure. Groups of female mice (six mice weighing 18–20 grams each) are injected intraperiteneally with bacteria which are thawed just prior to use and suspended in brain heart infusion with 4% brewers yeast (*Staphylococcus aureus*) or brain heart infusion (*Streptecoccus species*). Antibiotic treatment at six dose levels per drug is administered one hour and five hours after infection by either oral intubation or subcutaneous routes. Survival is observed daily for six days. ED$_{50}$ values based on mortality ratios are calculated using probit analysis. The subject compounds are compared against drug U-100592 as controls. The comparator drug U-100592 has been extensively evaluated in this animal model versus vancomycin, and has routinely been shown to be equipotent to vancomycin. The detailed information with respect to the structure and in vivo efficacy evaluations of U-100592 is summarized in *Upjohn Oxazolidinone Antibacterial Agents*, Posters Presented at the 35th Interscience Conference on Antimicrobial Agents and Chemotherapy, San Francisco, 17–20 September 1995. The data are shown in Table 1.

TABLE 1

| In Vivo Activity of Compounds Against *S. aureus* UC ® No. 9213 | | |
|---|---|---|
| Example No. | ED$_{50}$ (mg/kg) | U-100592 ED$_{50}$ (mg/kg) |
| 1 | 6.2 | 6.3 |
| 2 | 4.4 | 1.8 |
| 3 | 8.8 | 8.7 |
| 4 | 6.3 | 8.7 |

In order to more fully illustrate the nature of the invention and the manner of practicing the same, the following experimental examples are presented, but they should not be taken as limiting.

EXAMPLE 1

Preparation of (S)-N-[[3-[-3-fluoro-4-[4-(2-pyrimidinyl)-1-piperazinyl]phenyl-2-oxo-5-oxazolidinyl]methyl] acetamide.

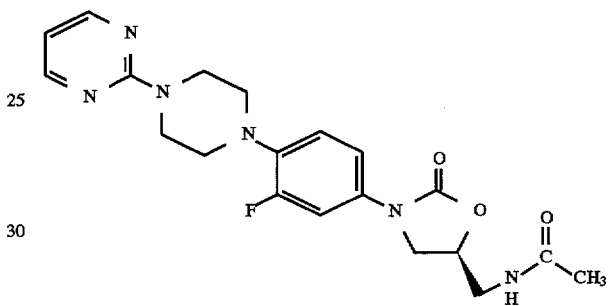

A three-neck round bottom flask is loaded with 20 g of (S)-N-[[3-[4-[3-fluoro-4-(1-piperazinyl)]phenyl]-2-oxo-5-oxazolidinyl]methyl]-acetamide hydrochloride. Dimethylacetamide (70 mL) is added, and the mechanically stirred suspension is immediately treated with 20.6 mL of diisopropylethylamine. The mixture is then treated with 6.76 g of 2-chloropyrimidine and stirred under a nitrogen atmosphere 24 hours at 25° C. The temperature of the reaction mixture is increased to 45° C. and the mixture is stirred an additional 48 hours. The mixture is cooled to 25° C., then it is diluted by dropwise addition of 200 mL of distilled water. The resulting suspension is filtered and the collected solid is washed with 200 mL of distilled water. The solid is dried in a stream of nitrogen and then it is dissolved in 1100 mL of a 9:1 (v/v) mixture of dichloromethane and absolute ethanol. This solution is stirred with 250 grams of silica gel for 5 minutes and then the mixture is filtered. The silica gel is eluted with 1500 mL of a 9:1 (v/v) mixture of dichloromethane and absolute ethanol. The flitrate and eluate are combined and the solvents are removed by evaporation at reduced pressure. The residual solid is dissolved in 900 mL of refluxing isopropanol and the resulting solution is decanted from a small amount of insoluble material. The volume of the solution is reduced to 300 mL by distillation at atmospheric pressure, and the resulting solution is stored 15 hours at 25° C. The precipitate is collected by filtration and washed with two 30 mL portions of isopropanol. After drying in a stream of nitrogen, the solid is suspended in 100 mL of distilled water and stirred vigorously while 25 mL of 3 N hydrochloric acid is added. The mixture is stirred until a clear solution forms. This solution is washed with two 100 mL portions of ethyl acetate. The aqueous phase is then diluted with 100 mL of distilled water and treated with 75 mL of 2 N dipotassium hydrogen phosphate solution while stirring vigorously. The resulting precipitate is collected by filtration and then it is washed with two successive 300 mL portions of distilled water. It is dried in a stream of nitrogen and ground to a fine powder with a mortar and pestle. The solid is dissolved in 1000 mL of tetrahydrofuran and the resulting solution is filtered. The flitrate is treated with 0.5 mL of ammonia-saturated methanol. The solvent is evaporated and the solid residue is washed with 300 mL of distilled water. The solid is collected by filtration and dried in a stream of nitrogen. It is dried further at 55° C. in a partial vacuum for 5 hours to give the desired compound as 11.9 g of a solid. Mass spectral analysis gives a molecular ion at m/e=414.

EXAMPLE 2

Preparation of (S)-N-[[3-[-3-fluoro-4-[4-(4-pyrimidinyl)-1-piperazinyl]phenyl-2-oxo-5-oxazolidinyl]methyl] acetamide.

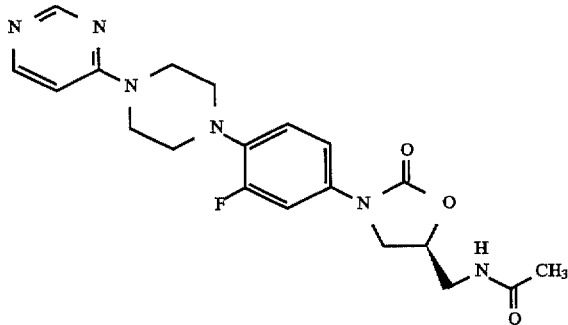

Step 1. Preparation of(S)-N-[[3-[-3-fluoro-4-[4-(4-(2-chloropyrimidinyl) -1-piperazinyl]phenyl-2-oxo-5-oxazolidinyl]methyl]acetamide.

A solution prepared by dissolving 0.50 g of (S)-N-[[3-[4-[3-fluoro-4-(1-piperazinyl)]phenyl]-2-oxo-5-oxazolidinyl] methyl]-acetamide hydrochloride and 0.371 mL of triethylamine in 5 mL of dimethylformamide is treated with 0.20 g of 2,4-dichloropyrimidine. The mixture is stirred 16 hours at 25° C. The mixture is diluted with 37 mL of ethyl acetate and 37 mL of distilled water, and it is stirred until almost all of the solids have dissolved. The mixture is filtered through a plug of glass wool and then the phases are separated. The organic phase is washed with brine and dried over magnesium sulfate. The solution is filtered and the solvent is evaporated at reduced pressure. The residue is suspended in 25 mL of toluene and the mixture is stirred for 2 hours. The mixture is filtered and the filtrant is washed with 10 mL of toluene. This solid is dried to give 0.499 g of a white powder. Mass spectral analysis gives a molecular ion at m/e 448.
Step 2. Preparation of (S)-N-[[3-[-3-fluoro-4-[4-(4-pyrimidinyl)-1-piperazinyl]phenyl-2-oxo-5-oxazolidinyl] methyl]acetamide.

A suspension of the product of Step 1, Example 2 (0.15 g) in 2:1 absolute ethanol/ethyl acetate is agitated and treated with 0.3 mL of 3.0 N hydrochloric acid. To the resulting solution is added a catalytic amount of 5% palladium on carbon and the mixture is agitated under an atmosphere of 50 psi hydrogen gas for 3 days. The catalyst is removed by filtration, and the solvent is evaporated at reduced pressure. The residue is partitioned between ethyl acetate and 1.0 molar dipotassium hydrogen phosphate solution. The aqueous phase is washed with two additional portions of ethyl acetate, and the combined organic extracts are washed with brine and dried over magnesium sulfate. The solution is filtered and the solvent is evaporated at reduced pressure. The residue is chromatographed on silica gel eluting with 93:7 (v/v) dichloromethane/absolute ethanol. The solid thus obtained is washed with a small volume of hexanes and dried (60° C./20 torr/12 hours) to give 52 mg of the title compound. Mass spectral analysis gives a molecular ion at m/e=414.

EXAMPLE 3

Preparation of (S)-N-[[3-[-3-fluoro-4-[4-(3-pyridazinyl)-1-piperazinyl]phenyl-2-oxo-5-oxazolidinyl]methyl] acetamide.

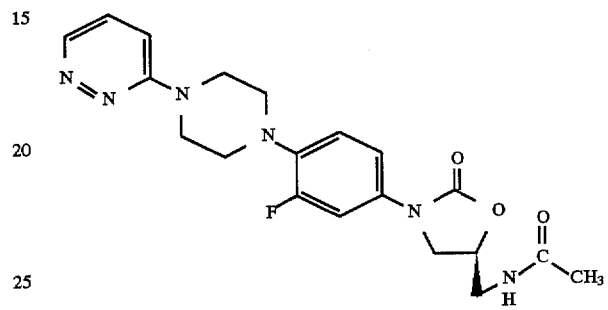

Step 1. Preparation of (S)-N-[[3-[-3-fluoro-4-[4-(3-(6-chloropyridazinyl))-1-piperazinyl]phenyl-2-oxo-5-oxazolidinyl]methyl]acetamide Triethylamine (0.80 mL) is added to a dimethylformamide (15 mL) solution of (S)-N-[[3-[4-[3-fluoro-4-(1-piperazinyl)]phenyl]-2-oxo-5-oxazolidinyl]methyl]-acetamide hydrochloride (1.023 g) and 3,6-dichloropyridazine (0.435 g). The reaction mixture is placed under nitrogen atmosphere and is stirred overnight. The temperature is then gradually increased to 70° C., and the mixture is stirred at this temperature for seven days. The mixture is cooled to 25° C., then water (100 mL) and ethyl acetate (100 mL) are added. This mixture is filtered. The phases are separated, and the organic layer is dried (MgSO₄) and evaporated to give 0.543 g of crude product. This material is chromatographed on a medium pressure silica column (2.5×28 cm, packed and eluted with 3% MeOH/ CH₂Cl₂) to give 0.279 g of partially purified product. This is further purified on a second medium pressure silica column (2.5×28 cm, packed with 5% MeOH/CH₂Cl₂, eluted with 1 L 5% and 500 mL 10% MeOH/CH₂Cl₂) to give 0.114 g (9%) of the title compound as a yellow. solid. Mass spectral analysis of this material gave a molecular ion peak at m/e 448.
Step 2. Preparation of (S)-N-[[3-[-3-fluoro-4-[4-(3-pyridazinyl)-1-piperazinyl]phenyl-2-oxo-5-oxazolidinyl] methyl]acetamide.

A flask containing a methanol (10 mL) and ethyl acetate (10 mL) solution of the product of Step 1, Example 5 (0.228 g) is alternately evacuated and filled with nitrogen three times. Palladium black (0.091 g) is then added. The flask is evacuated and filled with nitrogen two more times. It is then evacuated and filled with hydrogen three times, and the mixture is stirred 20 h under an atmosphere of hydrogen. The hydrogen is removed from the flask, and the mixture is placed under a nitrogen atmosphere. The solution is filtered through a plug of diatomaceous earth, which is carefully washed with more solvent. The flitrates are combined and the solvent is evaporated at reduced pressure. This crude product is purified on a preparative TLC plate (1000μ, eluted with 4% then 8% MeOH/CH$_2$Cl$_2$) to give 0.114 g of the title compound as a white solid, mp 207°–208° C.

EXAMPLE 4

Preparation of (S)-N-[[3-[-3-fluoro-4-[4-(3-(6-methylpyridazinyl))-1-piperazinyl]phenyl-2-oxo-5-oxazolidinyl]methyl]acetamide.

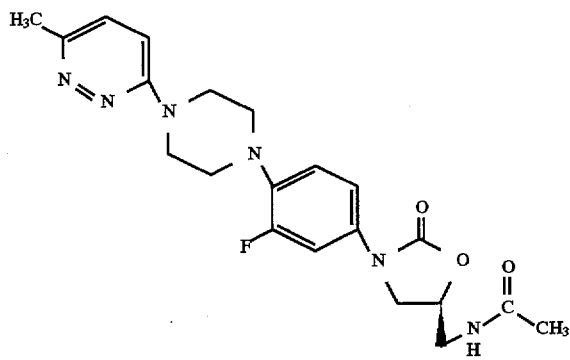

Triethylamine (0.6 mL) is added to a dimethylpropyleneurea (3 mL) solution of (S)-N-[[3-[4-[3-fluoro-4-(1-piperazinyl)]phenyl]-2-oxo-5-oxazolidinyl]methyl]-acetamide hydrochloride (0.546 g) and 3-chloro-6-methyl pyridazine (0.254g). The reaction mixture is stirred 1 day at ambient temperature, 6 hours at 50° C., and 2 days at 90° C. under a nitrogen atmosphere. The solvent is removed via a bulb-to-bulb distillation, and the crude material is purified on a medium pressure silica column (2.3×26 cm, packed and eluted with 3% MeOH/CH$_2$Cl$_2$) to give 0.181 g of slightly impure product. This material is further purified on a preparative TLC plate (1000μ, eluted with 4% MeOH/CH$_2$Cl$_2$ three times) to give 0.060 g of the title compound as solid, mp 237°–238° C.

We claim:

1. A compound of the Formula I

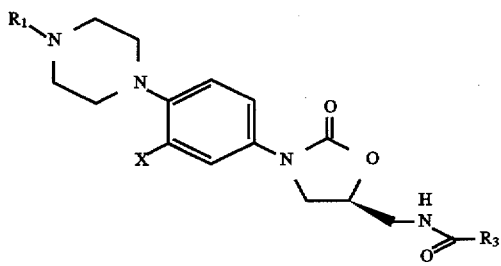

I or pharmaceutically acceptable salts thereof wherein R$_1$ is

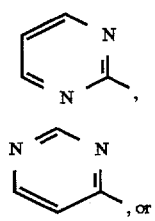

(a)

(b)

, or

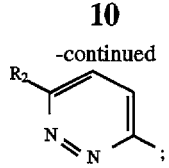

(c)

R$_2$ is (a) hydrogen, or (b) C$_{1-4}$ alkyl;

R$_3$ is (a) C$_{1-4}$ alkyl, (b) C$_{3-6}$ cycloalkyl, (c) C$_{1-4}$ alkoxy, (d) C$_{1-4}$ alkylamino, or (e) C$_{1-4}$ dialkylamino; and X is (a) hydrogen; or (b) fluoro.

2. The compound of claim 1 wherein R$_1$ is 3-pyridazinyl.

3. The compound of claim 1 wherein R$_2$ is methyl.

4. The compound of claim 1 wherein R$_3$ is methyl.

5. The compound of claim 1 wherein X is fluoro.

6. The compound of claim 1 which is an optically pure enantiomer having the S-configuration at C5 of the oxazolidinone ring.

7. The compound of claim 1 which is:

(a) (S)-N-[[3-[-3-fluoro-4-[4-(2-pyrimidinyl)-1-piperazinyl]phenyl-2-oxo-5-oxazolidinyl]methyl] acetamide;

(b) (S)-N-[[3-[-3-fluoro-4-[4-(4-pyrimidinyl)-1-piperazinyl]phenyl-2-oxo-5-oxazolidinyl]methyl] acetamide;

(c) (S)-N-[[3-[-3-fluoro-4-[4-(3-pyrimidinyl)-1-piperazinyl]phenyl-2-oxo-5-oxazolidinyl]methyl] acetamide; or (d) (S)-N-[[3-[-3-fluoro-4-[4-(3-(6-methylpyridazinyl))-1-piperazinyl]phenyl-2-oxo-5-oxazolidinyl]methyl] acetamide.

8. A method for treating microbial infections in patients comprising:

administering to a patient in need thereof an effective amount of a compound of Formula I as shown in claim 1.

9. The method of claim 8 wherein said compound of Formula I is administered orally, parenterally or topically in a pharmaceutical composition.

10. The method of claim 8 wherein said compound of Formula I is administered orally in a pharmaceutical composition.

11. The method of claim 8 wherein said compound is administered in an amount of from about 0.1 to about 100 mg/kg of body weight/day.

12. A pharmaceutical composition comprising a compound of claim 1 and a pharmaceutically acceptable carrier.

* * * * *